US012778625B2

(12) United States Patent
Nahum et al.

(10) Patent No.: US 12,778,625 B2
(45) Date of Patent: Nov. 3, 2026

(54) GUIDE DEVICE FOR A MEDICAL NEEDLE

(71) Applicant: Quantum Surgical, Montpellier (FR)

(72) Inventors: Bertin Nahum, Castelnau-le-Lez (FR); Fernand Badano, Lyons (FR); Lucien Blondel, Montpellier (FR); Sébastien Olive, Montpellier (FR)

(73) Assignee: Quantum Surgical, Montpellier (FR)

(*) Notice: Subject to any disclaimer, the term of this patent is extended or adjusted under 35 U.S.C. 154(b) by 780 days.

(21) Appl. No.: 17/600,983

(22) PCT Filed: Mar. 31, 2020

(86) PCT No.: PCT/EP2020/059131
§ 371 (c)(1),
(2) Date: Oct. 1, 2021

(87) PCT Pub. No.: WO2020/201286
PCT Pub. Date: Oct. 8, 2020

(65) Prior Publication Data

US 2022/0192699 A1 Jun. 23, 2022

(30) Foreign Application Priority Data

Apr. 4, 2019 (FR) ....................................... 1903636

(51) Int. Cl.
*A61B 17/34* (2006.01)
*A61B 34/30* (2016.01)

(52) U.S. Cl.
CPC .......... *A61B 17/3403* (2013.01); *A61B 34/30* (2016.02); *A61B 2017/3409* (2013.01)

(58) Field of Classification Search
CPC ................ A61B 17/3403; A61B 34/30; A61B 2017/3409; A61B 5/05; A61B 6/12;
(Continued)

(56) References Cited

U.S. PATENT DOCUMENTS 2,324,415 A 7/1943 Moss
5,280,427 A * 1/1994 Magnusson ............ A61B 90/11 600/407

(Continued)

FOREIGN PATENT DOCUMENTS

CA 2055486 C 11/1996
CN 101099673 A 1/2008

(Continued)

OTHER PUBLICATIONS

International Search Report for PCT/EP2020/059131, dated Aug. 14, 2020, 4 pages.

*Primary Examiner* — Shaun L David
*Assistant Examiner* — Cherie M Poland
(74) *Attorney, Agent, or Firm* — Troutman Pepper Locke LLP; Scott D. Wofsy; Michael J. Pollack

(57) ABSTRACT

The device (20) for guiding a needle includes a tool-holder (21) intended to be fixed to the end of a medical assistance robotic arm (10), said tool-holder (21) supporting a needle guide (22); the needle guide includes two jaws (30, 40) including a respective groove (35, 45), said two grooves extending along parallel longitudinal axes, said jaws (30, 40) being supported by the tool-holder so as to allow mobility in rotation of the jaws (30, 40) relative to one another between a position termed the "guiding position" in which the grooves (35, 45) are adjacent and define a duct (23) for guiding a needle and a position termed the "disengaged position" in which the grooves (35, 45) are moved away from one another and define a needle lateral disengagement zone.

20 Claims, 5 Drawing Sheets

(58) Field of Classification Search

CPC ......... A61B 17/34; A61B 19/26; A61B 19/22; A61B 2017/00911; A61B 2017/3405; A61B 2019/5238; A61B 2034/2059; A61B 2034/2055; A61B 2090/062; A61B 2090/3937; A61B 90/11; A61B 90/00; A61B 34/20; A61B 34/70; A61M 5/3287

See application file for complete search history.

(56) References Cited

U.S. PATENT DOCUMENTS

| | | | | |
|---|---|---|---|---|
| 8,840,627 | B2 * | 9/2014 | De Mathelin | A61B 17/3403 606/130 |
| 9,259,195 | B2 * | 2/2016 | Yanof | A61B 6/12 |
| 2004/0065341 | A1 | 4/2004 | La Fauci | |
| 2006/0026762 | A1 | 2/2006 | Hornbach et al. | |
| 2006/0161136 | A1 * | 7/2006 | Anderson | A61B 34/37 606/1 |
| 2006/0264963 | A1 | 11/2006 | Reed et al. | |
| 2008/0218948 | A1 | 9/2008 | Lai et al. | |
| 2010/0187782 | A1 | 7/2010 | Facey et al. | |
| 2012/0022554 | A1 | 1/2012 | Paik et al. | |
| 2015/0128405 | A1 * | 5/2015 | Zhang | B25J 15/0028 29/559 |
| 2016/0166354 | A1 | 6/2016 | Stulpe et al. | |
| 2016/0249991 | A1 * | 9/2016 | Glozman | A61B 17/3403 606/130 |
| 2016/0262913 | A1 | 9/2016 | Kling et al. | |
| 2019/0125459 | A1 * | 5/2019 | Shelton, IV | G16H 40/63 |
| 2020/0015807 | A1 * | 1/2020 | Limon | A61B 17/0469 |

FOREIGN PATENT DOCUMENTS

| | | | | |
|---|---|---|---|---|
| CN | 101411630 | A | 4/2009 | |
| CN | 101612053 | A | 12/2009 | |
| CN | 201642328 | U | 11/2010 | |
| CN | 102988109 | A | 3/2013 | |
| CN | 103037799 | A | 4/2013 | |
| CN | 103068535 | A | 4/2013 | |
| CN | 104637859 | A | 5/2015 | |
| CN | 105125290 | A | 12/2015 | |
| CN | 204828935 | U | 12/2015 | |
| CN | 105284629 | A | 2/2016 | |
| CN | 105411678 | A | 3/2016 | |
| CN | 105692502 | A | 6/2016 | |
| CN | 205363932 | U | 7/2016 | |
| CN | 106926062 | A | 7/2017 | |
| CN | 108290596 | A | 7/2018 | |
| CN | 108814740 | A | 11/2018 | |
| CN | 209186880 | U | 8/2019 | |
| DE | 202012010230 | U1 | 10/2013 | |
| EP | 0666209 | A1 | 8/1995 | |
| EP | 1621171 | A1 | 2/2006 | |
| EP | 3054862 | A1 | 8/2016 | |
| EP | 3318213 | A1 | 5/2018 | |
| FR | 3043970 | A1 | 5/2017 | |
| GB | 2440802 | A | 2/2008 | |
| JP | 2009509654 | A | 3/2009 | |
| WO | 9107922 | A1 | 6/1991 | |
| WO | WO-2011161304 | A1 * | 12/2011 | B25J 9/1694 |
| WO | WO-2012018816 | A2 * | 2/2012 | A61B 34/30 |
| WO | 2013192598 | A1 | 12/2013 | |
| WO | 2016190575 | A1 | 12/2016 | |
| WO | 2018055621 | A1 | 3/2018 | |

* cited by examiner

[Fig. 1]
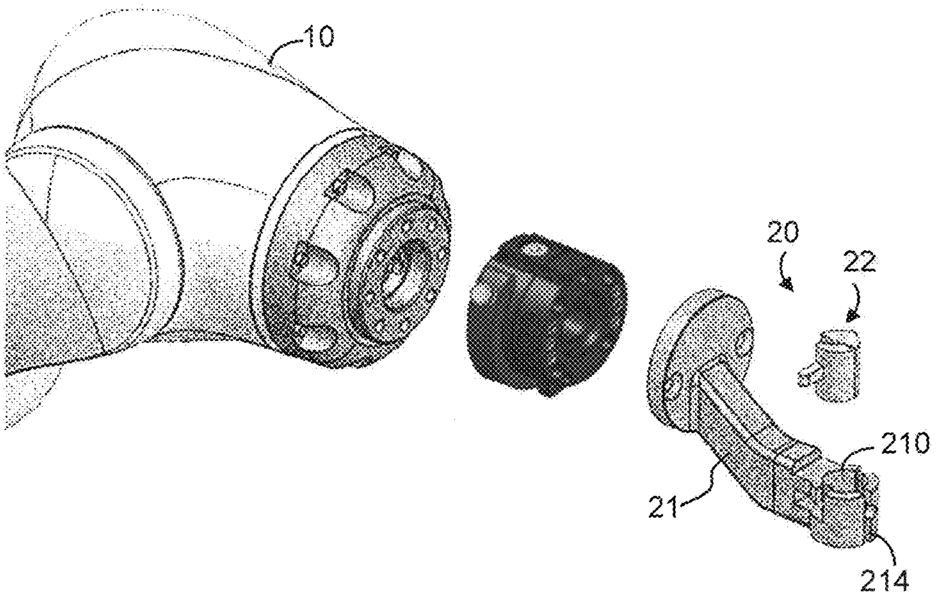
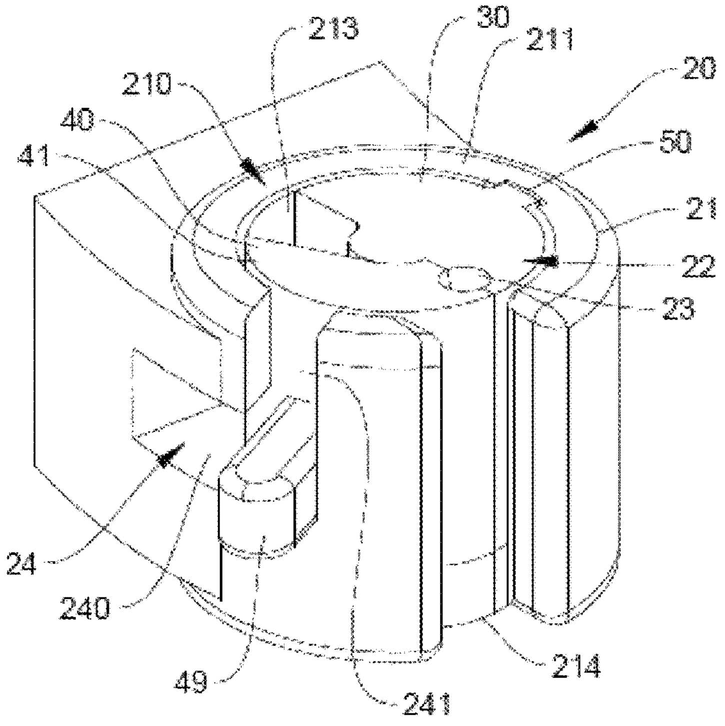
FIG. 2

[Fig. 3]
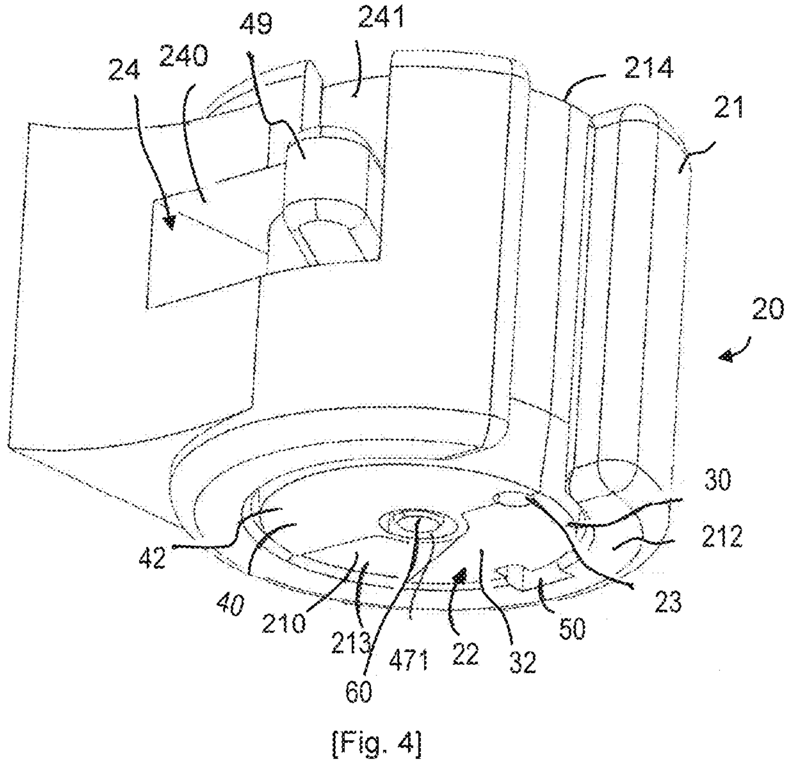
[Fig. 4]
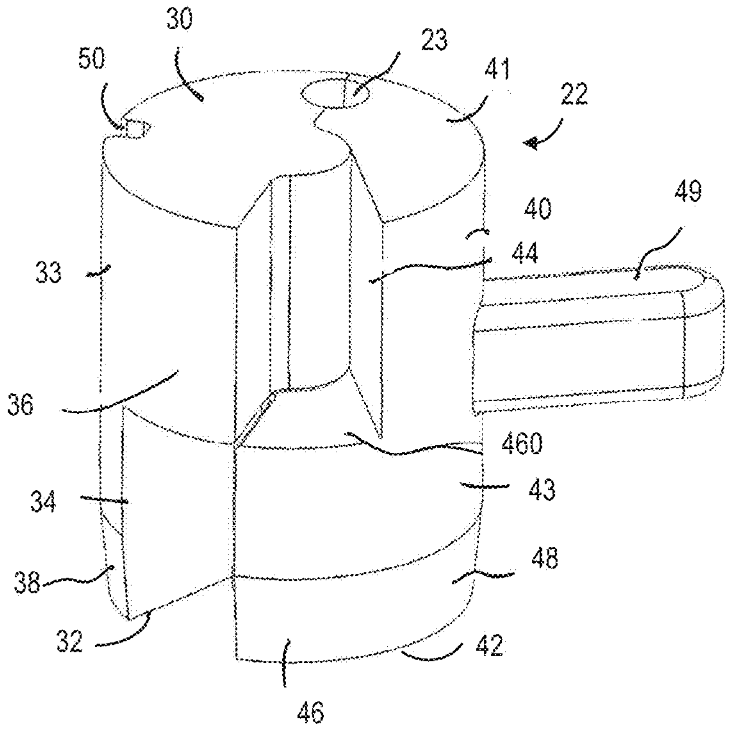

[Fig. 7]
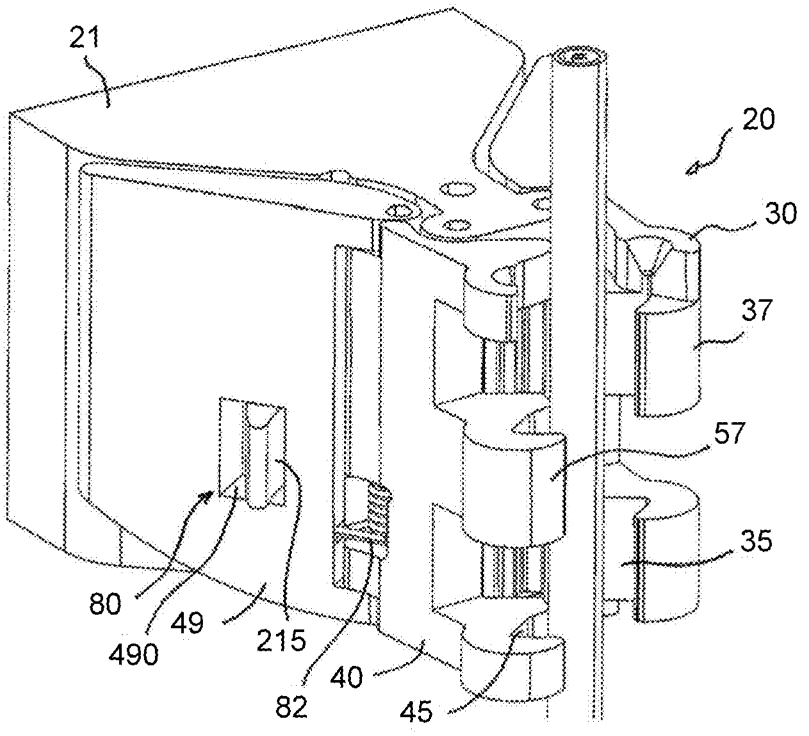
[Fig. 8]
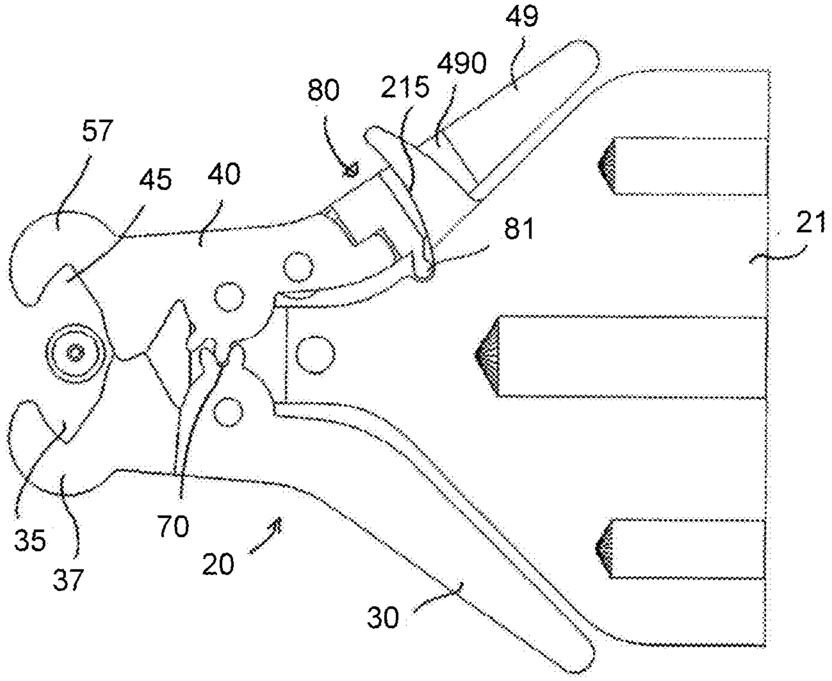

[Fig. 9]
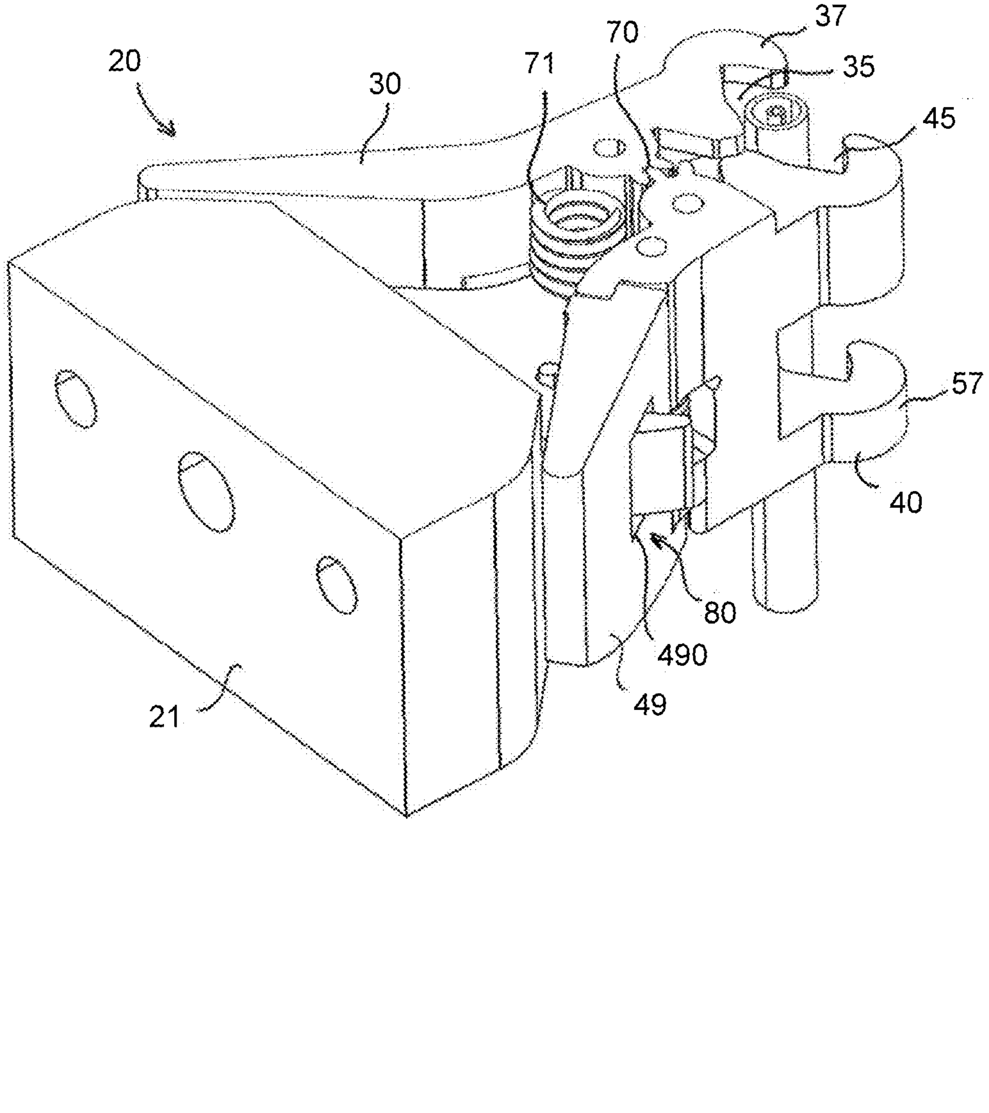

GUIDE DEVICE FOR A MEDICAL NEEDLE

CROSS-REFERENCE TO RELATED APPLICATIONS

This application is a National Stage of PCT/EP2020/059131, filed Mar. 31, 2020, which claims priority to French Patent Application No. 1903636, dated Apr. 4, 2019, the disclosures of each of which are hereby incorporated by reference in their entireties.

TECHNICAL FIELD OF THE INVENTION

The invention relates to medical equipment and lies in the field of medical equipment mounted at the end of a medical assistance robotic arm. The present invention more particularly concerns a device for guiding a medical needle intended to be fixed to a tool-holder of a robotic arm.

PRIOR ART

Surgical treatments using the surgical technique known as “minimally invasive surgery” enable an operator, typically a surgeon, to reach a target anatomical zone of a patient by the insertion of long and thin instruments into an incision of short length, for example of the order of one centimetre, produced in the body of the patient.

In the context of some operations, those instruments may be one or more needles or rigid cylindrical instruments (for example antennas, electrodes, cannulas) intended to be inserted into the body of a patient to a certain depth to reach the target anatomical zone.

If the needle is inserted entirely manually by the operator, the result of the treatment is greatly dependent on their skill. It is difficult to achieve high accuracy and there is a high risk of medical errors resulting from this lack of accuracy, which can injure the patient.

The accuracy of the operation can be improved thanks to the use of robotic arms remote-controlled by an operator. This type of robotic arm remains partially dependent on the skill of the operator and may necessitate continuous imaging of the patient, which obliges the patient to be subjected to a certain dose of radiation.

In order to improve further the accuracy of the insertion gesture and to limit the doses of radiation to which the patient and the medical personnel are subjected, it is possible to use a robotic arm controlled automatically.

The robotic arm carries at its end a device for guiding a needle.

The operator communicates to the robotic arm a coordinate of a target anatomical zone of the patient to be reached and the arm is controlled so as to move the needle guide device in front of the target anatomical zone. The needle is then inserted by an operator into the guide device so as to reach the target anatomical zone. For the needle to reach that zone accurately it is necessary to control the position of the translation axis of the needle within the guide device. It is therefore essential to master all movement of the guide device and therefore the arm.

Controlling the movement is all the more important when the treatment necessitates the sequential insertion of needles into the target anatomical zone. In this case the needle guide device must be immobile during the insertion of each needle so that the position of the translation axis of said needle is preserved and released once the needle has been inserted into the target anatomical zone without moving the needle.

In fact, any uncontrolled movement of the needle once it is inserted in the target anatomical zone is liable to injure the patient.

There is therefore a need on the one hand to guide the insertion of at least one needle along a translation axis the position of which is preserved until the needle reaches a target anatomical zone and on the other hand to release the device guiding said needle when the latter has been inserted in the target anatomical zone with no risk of moving said needle.

Furthermore, there also exists a need to know the length of the needle inserted in the body of the patient.

Finally, there is a need to guide the insertion of at least two needles of different diameter with the same guide device during the same medical treatment or during separate medical treatments; each needle having to be guided along the same translation axis, the position of which is preserved, until it reaches a target anatomical zone and also having to be able to be disengaged from the guide device when it has been inserted in the target anatomical zone with no risk of it being moved.

SUMMARY OF THE INVENTION

An objective of the present invention is to address the aforementioned needs and to this end the invention concerns a device for guiding the needle, including a tool-holder intended to be fixed to the end of a medical assistance robotic arm. The tool-holder supports a needle guide. The needle guide includes a first jaw and a second jaw including a respective groove, said two grooves extending along parallel longitudinal axes. Said first and second jaws are supported by the tool-holder so as to allow mobility in rotation of the first and second jaws relative to one another between a position termed the “guide position” in which the grooves are adjacent and define a duct for guiding a needle and a position termed the “disengaged position” in which the grooves are moved away from one another and define a needle lateral disengagement zone.

When the guide device occupies the guiding position, a needle can be guided in movement in translation through the guide duct until it reaches a target anatomical zone of a patient.

The guide duct is configured so as to allow a needle only one degree of freedom of movement in translation.

When the jaws are in the disengaged position, by moving in translation in a direction away from the disengagement zone the guide device is free to disengage laterally a needle that has reached a target anatomical zone. This lateral disengagement occurs for example at the end of a medical operation if only one needle has to be introduced into the target anatomical zone or during a medical operation if an additional needle has to be introduced into the target anatomical zone.

It should be noted that by an abuse of language the present text states that the guiding and disengaged positions are occupied by the needle guide and by the jaws.

Thanks to the features of the present invention, a needle can be disengaged from the needle guide without contact so that it remains fixed in position in the target anatomical zone.

Unwanted movement of the needle that could injure a patient is therefore prevented.

Thanks to these features, the guide device enables the successive insertion during the same medical operation of a plurality of needles of the same diameter using the same guide device to reach a target anatomical zone.

In particular embodiments, the invention also has the following features separately or in each of their technically operative combinations.

In particular embodiments of the invention, the first jaw or the second jaw comprises a handle for manipulating it by the solicitation whereof said first jaw or said second jaw is driven in movement relative to the other jaw.

In particular embodiments of the invention, the tool-holder comprises a housing extending longitudinally between two end openings and in which the needle guide is engaged. The tool-holder includes an axial through-opening extending from one to other of said end openings along an axis parallel to the longitudinal axis of the housing, the axial through-opening facing the lateral disengagement zone when the jaws are in the disengaged position.

Accordingly, once a needle has been guided until it reaches a target anatomical zone it can be disengaged from the guide device without contact so as to remain fixed in position in the target anatomical zone.

In particular embodiments of the invention, the first and second jaws are respectively formed by a fixed jaw and by a mobile jaw.

In particular embodiments of the invention, the fixed jaw is engaged in the housing, said fixed jaw and said housing having on their respective facing surfaces nesting elements cooperating with one another to immobilise said fixed jaw against rotation relative to the tool-holder.

The nesting elements are able to cooperate directly with one another; this is the case for example if the nesting elements are respectively formed by a groove and a tongue. The elements may alternatively cooperate indirectly with one another; this is the case for example if the nesting elements are formed by grooves in which a key or a pin is inserted.

The nesting elements advantageously have a poka yoke function during insertion of the needle guide into the housing.

In particular embodiments of the invention, the nesting elements are formed by respective complementary shape reliefs including:

- a relief extending longitudinally on a surface termed the "external surface" of the fixed jaw, and
- a relief extending longitudinally on a surface termed the "internal wall" of the housing.

These reliefs may be formed by a tongue and by a groove.

Thanks to the nesting elements, the fixed jaw is immobilised in a simple and reliable manner.

In particular embodiments of the invention, the first and second jaws are removably fixed to one another. They are preferably removably engaged in the housing of the tool-holder.

A feature of this kind aims in particular to enhance the efficacy of the sterilisation of the guide device, each component of said device being sterilisable individually.

In particular embodiments of the invention, the fixed jaw is formed in one piece with the tool-holder; the fixed jaw and the tool-holder therefore form a one-piece component.

In particular embodiments of the invention, the tool-holder comprises a through-opening extending radially relative to the housing. The first or second jaw includes a handle for manipulating it extending through the opening and when solicited by which said first or second jaw is driven in movement in the housing. The opening advantageously forms a path guiding the manipulation handle.

In particular embodiments of the invention, the opening includes a portion extending axially relative to the housing, said portion opening onto a surface of the tool-holder termed the "upper face" flush with one of the end openings of said housing.

Consequently, one of the jaws (where applicable both jaws depending on the particular embodiment of the invention) can be detached from the tool-holder in order to sterilise each component of the guide device individually and thereby to enhance the efficacy of the sterilisation of the guide device.

Thanks to this feature, the components of the guide device can also be replaced individually.

In particular embodiments of the invention, the first and second jaws include a respective axial shoulder. The axial shoulders have complementary profiles by means of which they cooperate with one another.

The first and second jaws rest against one another via their axial shoulders, said shoulders being at least partly interleaved with one another.

This feature advantageously favours guiding rotation of the second jaw in the housing.

The axial shoulders may advantageously constitute an abutment for the angular movement of the second jaw.

In particular embodiments of the invention, the first and second jaws are removably interconnected by means of a rod extending longitudinally from either the first jaw or the second jaw through an axial housing formed in the axial shoulder of the other jaw. The jaws are interconnected by a mechanical connection allowing only one degree of freedom in rotation.

Thanks to the rod, the rotation axes of the jaws are coaxial.

This feature, over and above participating in enhancing the efficacy the sterilisation of the first and second jaws, enables rapid fixing and detachment of said jaws.

In particular embodiments of the invention, the guide device includes an optical navigation system including reference optical elements mechanically connected to each of the first and second jaws and a reading module determining the position of each reference optical element, said navigation system being intended to be connected to a control unit configured to determine the position of said first and second jaws on the basis of information relating to the position of the optical elements transmitted by said optical navigation system.

Thanks to these features, it is possible to determine automatically the position of the jaws within the tool-holder.

In particular embodiments of the invention, the guide device includes a sensor housed in one of the grooves and configured to determine the length of the travel of a needle through the guide duct when the jaws are in the guiding position.

The sensor can advantageously be connected to the control unit which is configured to determine the position the position of said needle relative to said target anatomical zone of the patient on the basis of the information relating to the length of the travel of a needle inserted in the guide duct and on the basis of the position of a target anatomical zone of the patient relative to the position of the needle guide.

Also within the scope of the present invention is a needle guide device in combination with some or all of the features referred to hereinabove or hereinafter in which the needle guide includes a movement transmission member connected to the jaws and synchronising the angular movement of the jaws relative to one another.

Thanks to this feature the two jaws are moved angularly symmetrically to one another.

In other words, during the rotation of one jaw, the transmission member drives the rotation of the other jaw with an identical angular movement.

A needle can therefore be gripped by the grooves without modifying the position of its longitudinal axis which makes it possible to prevent errors in positioning the needle, for example when changing needle.

Furthermore, this feature enables use of needles of different diameter.

In particular embodiments of the invention, the guide device includes an elastic member arranged against at least one of the jaws so as to urge the first and second jaws in rotation toward their guiding position.

This feature is advantageous in that it makes it possible to prevent any movement of the needle guide in the disengaged position and therefore any accidental movement of the needle.

Furthermore, this feature enables systematic driving of the jaws in the guiding position and therefore eliminates the need for an operator to carry out this operation manually.

In particular embodiments of the invention, each jaw includes at least one tooth at the level of the grooves, said at least one tooth being adapted to interpenetrate when the needle guide is in the guiding position.

Each jaw more particularly includes at least one tooth, said teeth being arranged face to face. The grooves are formed transversely in the respective teeth of the jaws.

This feature enables distribution along said needle of the clamping forces applied to the needle by the jaws, in particular by the teeth, and thus participation in guaranteeing the stability of the needle when it is engaged in the guide duct.

In particular embodiments of the invention, the grooves have a V-shape cross-section.

Thus for a given tool-holder position a needle is gripped in the guide duct between the two jaws in exactly the same way whatever its diameter, the position of the longitudinal axis of said needle not depending on its diameter. It is therefore possible to change needle during an operation and to preserve the same axis of movement in translation of the needle whatever its diameter.

In particular embodiments of the invention, the needle guide device comprises a mechanism for locking the needle guide in the guiding position. The locking mechanism is configured to immobilise the first jaw or the second jaw against rotation when the latter pivots beyond a predetermined angular position.

This feature advantageously enables retention of the needle by the jaw and more particularly prevention of all angular relative movement of the needle whilst allowing movement in translation along its longitudinal axis.

Thus any accidental transverse solicitation of the needle cannot lead to a movement of the needle liable to disengage the needle from the guide duct and in the end to injure a patient.

In particular embodiments of the invention, the locking mechanism includes:

- a pivot connection connecting the manipulation handle to the first jaw or to the second jaw and allowing one degree of freedom in rotation of said handle relative to said jaw between two extreme angular positions,
- a lip extending from the manipulation handle toward the tool-holder, and
- an elastic member soliciting said handle in rotation toward one of its extreme angular positions so that the lip is braced against a contact surface of the tool-holder when the first and second jaws are in the guiding position.

In other words, the elastic member solicits the manipulation handle so as to generate the phenomenon of bracing the lip against the contact surface of the tool-holder.

This feature enables immobilisation of the needle guide in the guiding position by simple mechanical means.

Another advantage lies in the rapid unlocking of the needle guide to allow it to move into the disengaged position.

In fact, it is only necessary to apply a force opposing the solicitation of the manipulation handle by the elastic member to reduce and/or to eliminate the friction causing the bracing phenomenon.

According to another aspect, the present invention also concerns a robotic arm including at one of its ends a needle guide device as described above.

The robotic arm comprises a control unit intended to be receive information relating to a position of the first jaw or of the second jaw from an optical navigation system of the needle guide device. The control unit is configured to determine the position of the mobile jaw and to command the configuration of the robotic arm in a given position according to the determined position of said jaw.

In particular embodiments of the invention, the control unit is configured so that:

- when it determines that the first jaw and the second jaw are in the guiding position, it prohibits all movement of the robotic arm, and
- when it determines that the first jaw and the second jaw are in the disengaged position, it allows movement of the robotic arm.

It is therefore not possible to modify the position of the guide device and therefore of the axis of movement in translation of a needle inserted in the guide duct.

This feature furthermore enables preservation of the position of the guide duct during a medical operation so as to guarantee the accuracy of the insertion of the needle into a target anatomical zone of the patient.

Furthermore, this feature makes it possible to prevent injuries that could be caused by accidental movement of the robotic arm carrying a needle guide in which a needle is inserted.

When the first and second jaws are in the disengaged position, the robotic arm is allowed to move so that it can be moved laterally with respect to the target anatomical zone of the patient in order to disengage the needle from the needle guide without it having any contact with the guide device. The needle therefore remains immobile during its disengagement.

BRIEF DESCRIPTION OF THE DRAWINGS

The invention will be better understood on reading the following description given by way of nonlimiting example and with reference to the following figures:

FIG. 1 represents an exploded perspective view of a robotic arm, a needle guide device according to a first embodiment and a tool changer providing the interface between the free end of the robotic arm and the guide device;

FIG. 2 represents a perspective view from above of the guide device from FIG. 1, the guide device including a tool-holder of which only a portion is shown and a needle guide that is shown in a position for guiding the needle;

FIG. 3 represents a perspective view from below of the guide device from FIG. 2;

FIG. 4 represents a perspective view from above of the needle guide of the guide device from FIG. 2;

FIG. 7 represents a perspective view of a second embodiment of a needle guide device;

FIG. 8 represents a sectional view of the needle guide device from FIG. 7;

FIG. 9 represents a perspective view of a cross section of the device from FIG. 7.

Figure 5:
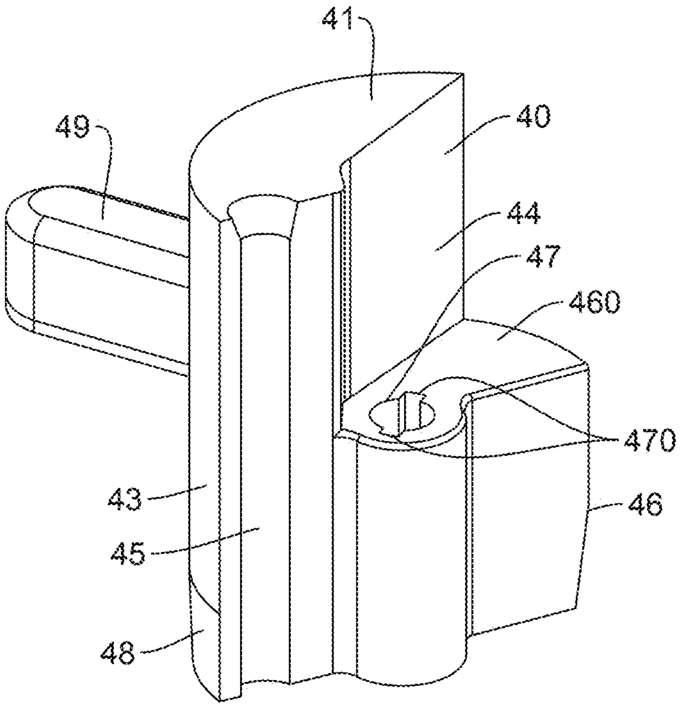
FIG. 5 represents a perspective view from above of a mobile jaw of the needle guide from FIG. 2.

In these figures reference numbers identical from one figure to another designate identical or analogous elements. Furthermore, for reasons of clarity, the drawings are not to scale unless otherwise indicated.

DESCRIPTION OF EMBODIMENTS

FIG. 1 shows a robotic arm 10 including at its free end a needle guide device 20 according to a first embodiment intended to assist an operator during a medical operation to introduce a needle into the body of a patient until it is inserted in a target anatomical zone. The robotic arm 10 preferably includes a tool changer at its free end providing the interface between said free end and the guide device 20.

The guide device 20 includes a tool-holder 21 intended to be fixed to the robotic arm 10 and a needle guide 22 cooperating with said tool-holder 21, as FIGS. 2 and 3 show.

The tool-holder 21 includes a housing 210 extending longitudinally between two end openings respectively opening onto a face termed the "upper face" 211 and onto a face termed the "lower face" 212 of the tool-holder 21. The housing 210 is defined between its two end openings by an internal wall 213.

The internal wall 213 has a cross section of circular shape in the preferred embodiment shown in FIGS. 1 to 3.

The needle guide 22 is engaged in the housing 210 and in the preferred embodiment of the invention includes two jaws 30, 40 fixed to one another in a manner free to rotate between a "guide position" in which said jaws 30, 40 define a duct 23 for guiding the needle and a "disengaged" position in which they define a needle lateral disengagement zone.

The jaws are generally referred to hereinafter as the "first jaw" 30 and the "second jaw" 40.

As FIGS. 1 to 3 show the tool-holder 21 includes an axial through-opening 214 extending from one to the other of the end openings of the housing 210 along an axis parallel to the longitudinal axis of the housing 210. The first jaw 30 and the second jaw 40 are advantageously disposed in the housing 210 so that when they are in the disengaged position the lateral disengagement zone faces the axial through-opening 214.

A needle inserted in the guide duct 23 when the first jaw 30 and the second jaw 40 are in the guiding position in order to introduce it into a target anatomical zone of a patient can therefore, by virtue of movement of said guide device 20, be withdrawn laterally from the guide device 20 when the first jaw 30 and the second jaw 40 occupy the disengaged position via the lateral disengagement zone and the axial through-opening 214.

In a first embodiment, when the needle guide 22 is engaged in the housing 210, the first jaw 30, termed the "fixed jaw" 30, is preferably immobilised relative to the tool-holder 21 and the second jaw 40, termed the "mobile jaw" 40, is preferably free to rotate relative to said fixed jaw 30 about a rotation axis parallel to the longitudinal axis of the housing 210.

Figure 6:
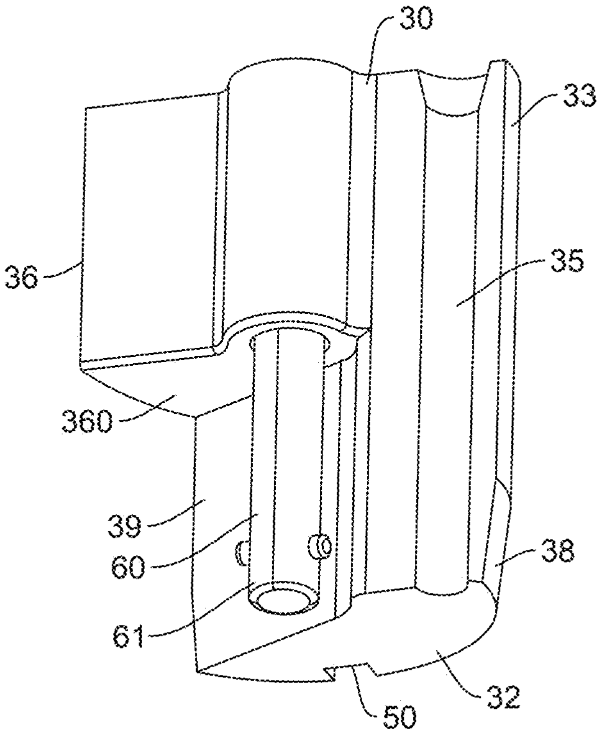
FIG. 6 represents a perspective view from below of a fixed jaw of the needle guide from FIG. 2.

As FIGS. 4 to 6 show, the fixed jaw 30 and the mobile jaw 40 more particularly extend between two ends respectively termed the "upper end" 31, 41 and the "lower end" 32, 42 along longitudinal axes parallel to the longitudinal axis of the housing 210. Said fixed jaw 30 and said mobile jaw 40 are respectively defined between their upper ends 31 and 41 and lower ends 32 and 42 by a peripheral surface of which a portion hereinafter termed the "extrados surface" 33, 43 is connected to a portion opposite it hereinafter termed the "intrados surface" 34, 44.

It should be noted that in the present text the relative terms "upper" and "lower" are defined so that a so-called "upper" element is situated above a so-called "lower" element, said relative terms being related to the position in which the robotic arm 10 and the guide device 20 are represented in FIGS. 1 to 3.

The extrados surfaces 33, 43 of the fixed jaw 30 and the mobile jaw 40 each have a cross section of circular shape and is arranged facing the internal wall 213 of the housing 210 when the needle guide 22 is engaged in the tool-holder 21.

As FIG. 4 shows, in the preferred embodiment of the invention the extrados surfaces 33, 43 of the fixed jaw 30 and the mobile jaw 40 are inscribed in a cylinder of circular cross section. The extrados surfaces 33, 43 and the internal wall 213 of the housing 210 are concentric when said fixed jaw 30 and said mobile jaw 40 are engaged in the housing 210.

In order to be engaged in the housing 210 the fixed jaw 30 and the mobile jaw 40 are sized so that the radius of the cross section of their extrados surface 33, 43 is smaller than the radius of the cross section of the internal wall 213 of said housing 210.

The intrados surfaces 34, 44 of the fixed jaw 30 and the mobile jaw 40 are arranged facing one another when the needle guide 22 is engaged in the tool-holder 21 and are sized so as to form a space for angular relative movement between said fixed jaw 30 and said mobile jaw 40.

Each fixed jaw 30 and mobile jaw 40 comprises on its intrados surface 34, 44 a groove 35, 45 extending along a longitudinal axis from its lower end 32, 42 to its upper end 31, 41. The grooves 35, 45 have respective cross sections of circular shape with identical dimensions. Alternatively, the grooves 35, 45 may have a cross section of polygonal shape.

The grooves 35, 45 are such that when the fixed jaw 30 and the mobile jaw 40 are in the guiding position said grooves 35, 45 are adjacent over all of their length and form the guide duct 23 for a needle and so that when the jaws occupy the disengaged position said grooves 35, 45 are moved apart and define between them the needle lateral disengagement zone.

The grooves 35, 45 are preferably arranged on a portion of the respective intrados surfaces 34, 44 of the fixed jaws 30 and mobile jaw 40 contained in a plane containing a diameter of the extrados surface 33, 43.

In the preferred embodiment of the invention the fixed jaw 30 and the housing 210 have on their facing respective surfaces, that is to say the extrados surface 33 of the fixed jaw 30 and the internal wall 213 of the housing 210, nesting elements 50 cooperating with one another to immobilise said fixed jaw 30 against rotation relative to the tool-holder 21.

The nesting elements 50 may advantageously allow one degree of freedom in movement in translation between the tool-holder 21 and the fixed jaw 30 so that the needle guide 22 can be removably engaged in the housing 210 of the tool-holder 21 as described in more detail hereinafter.

The nesting elements 50 are preferably formed by reliefs with complementary shapes respectively extending parallel to the longitudinal axis of the fixed jaw 30 and to the longitudinal axis of the housing 210. For example, these reliefs respectively take the form of a tongue and a groove, the tongue being, in the preferred embodiment, on the extrados surface 33 of the fixed jaw 30 and the groove being in the internal wall 213 of the housing 210, as FIG. 2 shows. Alternatively, the tongue is on the internal wall 213 of the housing 210 and the groove is in the extrados surface 33 of the fixed jaw 30.

The fixed jaw 30 is therefore immobilised in a simple and reliable manner.

The nesting elements 50 may alternatively take the form of grooves arranged longitudinally facing one another, respectively on the extrados surface 33 of the fixed jaw 30 and on the internal wall 213 of the housing 210, as FIG. 3 shows, and in which a key or a pin is intended to be engaged.

The nesting elements 50 have the advantage of a poka yoke function during insertion of the needle guide 22 into the housing 210.

As the FIGS. 5 and 6 views of the fixed jaw 30 on its own and the mobile jaw 40 on its own show, said fixed jaw 30 and said mobile jaw 40 each has an axial shoulder 36, 46 on its intrados surface 34, 44 through which said jaws cooperate with one another.

The axial shoulders 36, 46 of the fixed jaw 30 and the mobile jaw 40 extend away from one another from a bearing surface 360, 460 lying in a plane substantially orthogonal to the longitudinal axis of said jaws and as far as a surface flush with one or the other of the upper ends 31, 41 and lower ends 32, 42 of said fixed jaw 30 and said mobile jaw 40.

To be more precise, as FIGS. 4 and 6 show, the axial shoulder 36 of the fixed jaw 30 extends as far as a surface flush with its upper end 31 and the axial shoulder 46 of the mobile jaw 40 extends as far as a surface flush with its lower end 42. In other words, the axial shoulder 36 of the fixed jaw 30 is superposed on that of the mobile jaw 40.

In the preferred embodiment of the invention the bearing surfaces 360, 460 of the axial shoulders 36, 46 of the fixed jaw 30 and the mobile jaw 40 are each arranged equidistantly between the upper ends 31, 41 and lower ends 32, 42 of said jaws.

The axial shoulders 36, 46 rest one against the other via their respective bearing surfaces 360, 460 and have complementary profiles so that the fixed jaw 30 and the mobile jaw 40 are at least partly interleaved with one another.

The axial shoulders 36, 46 include a central portion through which the fixed jaw 30 and the mobile jaw 40 rest and bear one against the other continuously when they move between their disengaged and guiding positions, as FIG. 4 shows.

As FIGS. 5 and 6 show, the cross section of the intrados surface 34, 44 at the level of the central portion of each axial shoulder 36, 46 includes a segment of circular shape, said segment of circular shape being concentric with the cross section of the extrados surface 33, 43 and that of the internal wall 213.

The axial shoulders 36, 46 also include a respective lateral portion extending the central portion as far as a cylindrical surface in line with the extrados surface 33, 43 of the fixed jaw 30 and the mobile jaw 40. In other words, the cylindrical surface is inscribed in the same circular cylinder as the extrados surfaces 33, 43 of the fixed jaw 30 and the mobile jaw 40.

The lateral portion therefore has a general shape of a sector of a cylinder.

As FIGS. 5 and 6 show, the cross section of the intrados surface 34, 44 includes, at the level of the lateral portion of each axial shoulder 36, 46, a rectilinear segment extending the segment of circular shape as far as the extrados surface 33, 43.

The lateral portions of the axial shoulders 36, 46 are configured to constitute an abutment for angular movement of the mobile jaw 40 when the mobile jaw 40 is in the disengaged position.

The lateral portions are more particularly sized so that when the mobile jaw 40 is in the disengaged position they rest and bear against one another via their bearing surface 360, 460, the lateral portion of the axial shoulder 36 of the fixed jaw 30 coming into contact with the intrados surface 44 of the mobile jaw 40 and the lateral portion of the axial shoulder 46 of the mobile jaw 40 coming into contact with the intrados surface 34 of the fixed jaw 30.

The lateral portions of the axial shoulders 36, 46 are preferably sized to allow forty-five degrees of angular movement of the mobile jaw 40 between the guiding and disengaged positions.

This feature enables maximisation of the area of contact between the fixed jaw 30 and the mobile jaw 40 and therefore great accuracy in the movement of the mobile jaw 40 when it evolves between the disengaged and guiding positions.

The fixed jaw 30 and the mobile jaw 40 are preferably removably interconnected by means of a rod 60 extending longitudinally from the fixed jaw through a housing, termed the "coaxial housing" 47, extending axially and formed in the axial shoulder 46 of the mobile jaw 40, said mobile jaw 40 being free to pivot about the rod 60. In other words, a rod 60 extends in the axial housing 47 along a longitudinal axis coinciding with the axis of rotation of the mobile jaw 40.

As FIGS. 5 and 6 show, the axial housing 47 is more particularly formed through the central portion of the axial shoulder 46 of the mobile jaw 40.

The rod 60 extends between two ends one of which, termed the "upper end" is rigidly connected to the fixed jaw 30 and the other of which, termed "the lower end" is engaged in a freely rotatable manner in the axial housing 47.

Thanks to this feature, the fixed jaw 30 and the mobile jaw 40 can be detached from one another. An arrangement of this kind aims in particular to enhance the efficacy of sterilisation of a needle guide 22.

The lower end of the rod 60 advantageously includes an element blocking movement in translation adapted to prevent movement in translation between the fixed jaw 30 and the mobile jaw 40. This feature aims to prevent untimely unfastening of the fixed jaw 30 and the mobile jaw 40.

This kind of element blocking movement in translation may be formed on a pin 61 extending radially in said rod 60, as FIG. 6 shows. The pin 61 is intended to be arranged against the mobile jaw 40 so as to hold said mobile jaw 40 against the fixed jaw 30.

To be more precise, as FIG. 3 shows, the mobile jaw 40 advantageously includes a chamber 471 via which the axial housing 47 is open at its lower end 42 and said chamber 471 is adapted to receive the pin 61 when the fixed jaw 30 is fixed to the mobile jaw 40.

FIG. 5 shows two diametrically opposite axial grooves 470 extending over all of the length of the axial housing 47. These axial grooves 470 are intended to receive the sliding pin 61 when fixing or unfastening the fixed jaw 30 and the mobile jaw 40 to/from one another. Alternatively, depending on the length of the pin 61, the axial housing 47 of the mobile jaw 40 may include only one axial groove 470.

The axial grooves 470 are preferably arranged in the axial housing 47 so that fixing the fixed jaw 30 and the mobile jaw 40 to one another or unfastening them is possible only when said jaws are angularly positioned relative to one another equidistantly between the disengaged position and the guiding position, that is to say at mid-travel between the two extreme positions of the mobile jaw 40.

The mobile jaw 40 advantageously includes a handle 49 for manipulating it extending radially from its extrados surface 43. The manipulation handle 49 enables said mobile jaw 40 to be driven in movement in the housing 210 when solicited by an operator. This manipulation handle 49 is intended to move through an opening 24 formed in the tool-holder 21 and extending radially relative to the housing 210 by a portion hereinafter termed the "radial portion" 240.

The opening 24 therefore forms a path for guiding the manipulation handle 49 and extends over a sufficient length to enable angular movement of the mobile jaw 40 between the disengaged and guiding positions.

As shown in FIGS. 2 and 3 the radial portion 240 is extended, preferably at one of its ends, by a portion termed the "axial portion" 241 extending axially relative to the housing 210 until it opens onto the upper face 211 of the tool-holder 21.

A feature of this kind is advantageous because it enables the needle guide 22 to be unfastened from the tool-holder 21 by pivoting the manipulation handle 49 in the radial portion 240 of the opening 24 followed by movement in translation of said handle in the axial portion 241 along the longitudinal axis of the housing 210. The tool-holder 21 and the needle guide 22 can therefore be sterilised in an optimum manner.

Conversely, to engage the needle guide 22 in the tool-holder 21, an operator introduces the manipulation handle 49 through the axial portion 241 of the opening 24 by movement in translation of the needle guide 22 along the longitudinal axis of the housing 210 until it reaches the radial portion 240.

The axial portion is advantageously such that unfastening of the needle guide 22 from the tool-holder 21 is allowed only if the mobile jaw 40 is in the guiding position.

It is therefore possible to guide a needle axially directly after installing the needle guide 22 in the housing 210.

This prevents all risk of the needle jamming outside the guide duct 23, between the fixed jaw 30 and the mobile jaw 40, during actuation of said mobile jaw 40 toward its guiding position; such jamming possibly causing uncertain guidance of the needle that is potentially hazardous for a patient.

To facilitate, engaging the needle guide 22 in the housing 210 the fixed jaw 30 and the mobile jaw 40 may advantageously comprise a chamfer 38, 48 extending between their respective lower end 32, 42 and their respective extrados surface 33, 34.

In a variant of the first embodiment of the needle guide 20 not shown in the figures the tool-holder 21 and the fixed jaw form a one-piece component. In this embodiment of the invention the mobile jaw corresponds to the above description of it except that its axial shoulder extends from a bearing surface to a surface flush with the upper end of said mobile jaw.

In this embodiment of the invention the axial shoulder of the fixed jaw extends from a bearing surface to a surface flush with the lower end of said fixed jaw.

It is clear here that the axial shoulder of the mobile jaw is superposed on that of the fixed jaw, that is to say that of the tool-holder 21.

Furthermore, the rod is rigidly fixed to the mobile jaw and is engaged in a freely rotatable manner in the axial housing of the fixed jaw. Said axial housing includes two diametrically opposite axial grooves extending from the bearing surface of the axial shoulder to a chamber opening onto the lower face of said tool-holder 21. In an analogous manner to the preferred embodiment of the invention, the rod has at its lower end a movement in translation blocking element such as a pin that is intended to slide in the grooves when fixing or unfastening the mobile jaw to/from the tool-holder 21.

In this embodiment of the invention the tool-holder 21 comprises a sensor adapted to determine the length of the travel of the needle moving through the guide duct when the jaws are in the guiding position.

The sensor is advantageously connected to the control unit which determines the position of said needle relative to said target anatomical zone of the patient on the basis of information relating to the length of the travel of a needle inserted in the guide duct and on the basis of the position of a target anatomical zone of a patient relative to the position of the needle guide.

The sensor may be an optical sensor known in itself by the person skilled in the art, adapted to detect the movement of the needle introduced through the guide duct by capturing images. The sensor may equally be formed by a linear measurement sensor also known in itself by the person skilled in the art.

Alternatively the tool-holder 21 may incorporate a linear optical coder type sensor adapted to determine the travel of a graduated needle moving in the guide duct by reading the graduations on said needle.

A further alternative is for the sensor to take the form of a wheel driven by the needle when it is inserted through the duct, said wheel being associated with a revolution counter such as a tachometer. The diameter of the wheel being known by the control unit, said control unit is able to determine the length of needle inserted through the guide duct as a function of the angular displacement occurring during the movement of the needle.

FIGS. 7 to 9 represent a needle guide device 20 according to a second embodiment.

The guide device 20 according to this second embodiment conforms to the guide device 20 according to the first embodiment in that it also includes a tool-holder 21 and a needle guide 22 including first and second jaws 30 and 40 mobile relative to one another between a guiding position and a disengaged position.

Furthermore, in this second embodiment the second jaw 40, here termed the "driving jaw" 40, also includes a manipulation handle 49. However, the tool-holder 21 does not include an opening in which the manipulation handle 49 moves.

In this embodiment the first jaw 30 is termed the "driven jaw" 30.

In contrast to the first embodiment, in the second embodiment the driven jaw 30 and the driving jaw 40 are fixed to the tool-holder 21 so as to be mobile in rotation about respective different, that is to say non-coaxial, rotation axes. The rotation axes of the driven jaw 30 and the driving jaw 40 are preferably parallel to one another.

The tool-holder 21 includes a yoke comprising an "upper lug" and a "lower lug" between which the driven jaw 30 and the driving jaw 40 are arranged. Only the upper lug can be seen in FIG. 7.

The upper and lower lugs include a pair of orifices, the orifices of the two facing pairs receiving a fixing shaft, each fixing shaft being engaged in a through-housing of the driven jaw 30 or the driving jaw 40.

Each driven jaw 30 and driving jaw 40 is therefore free to pivot about the shaft with which it is associated.

As FIGS. 7 to 9 show, the needle guide advantageously includes a movement transmission member 70 connected to the driven jaw 30 and to the driving jaw 40 synchronising the angular movement of said driven jaw 30 and said driving jaw 40 relative to one another.

As shown in FIG. 8, the movement transmission member 70 is preferably formed by two meshing toothed wheel portions respectively arranged on the driven jaw 30 and the driving jaw 40.

Alternatively the movement transmission member 70 may be formed by a cam mechanism (not shown in the figures) in which a male part extending from one of the jaws, for example the driving jaw 40, cooperates with a female part extending from the other jaw, for example the driven jaw 30.

Thanks to this feature, the driven jaw 30 and the driving jaw 40 are driven in symmetrical angular movement, that is to say they move through the same angle.

A needle can therefore be gripped by the grooves 35, 45 without modifying the position of its longitudinal axis, which makes it possible, for example during a needle change, to avoid any needle positioning error.

Furthermore, this feature enables use of needles of different diameter. This feature preferably enables guiding of needles the diameter of which is between 11 G and 21 G inclusive.

An elastic member 71 is arranged against the driven jaw 30 and/or the driving jaw 40 so as to solicit said driven jaw 30 and said driving jaw 40 in rotation towards their guiding position, as FIG. 9 shows.

The elastic member 71 may more particularly be a torsion spring arranged between the driven jaw 30 and the driving jaw 40, opposite their groove 35, 45, and each end of which bears against said driven jaw 30 or said driving jaw 40. Alternatively, the elastic member 71 may be a compression spring.

This feature is an advantage in that it makes it possible to prevent movement of the needle guide 22 in the disengaged position and therefore accidental movement of the needle.

Furthermore, this feature enables systematic driving of the driven jaw 30 and the driving jaw 40 into the guiding position and therefore to eliminate the need for an operator to carry out this operation manually.

The driven jaw 30 and the driving jaw 40 advantageously include at the junction between their intrados surface 34, 44 and their extrados surface 33, 43 teeth 37, 57 adapted to interpenetrate when the needle guide 22 is in the guiding position.

As shown in FIGS. 7 to 9, each tooth 37, 57 therefore includes a segment of a groove 35, 45, said groove 35, 45 extending transversely relative to the teeth 37, 57.

These features enable distribution along said needle of the clamping forces applied to the needle by the driven jaw 30 and the driving jaw 40, in particular by the teeth 37, 57, and therefore participation in guaranteeing the stability of the needle when it is engaged in the guide duct 23.

The grooves 35, 45 preferably have a V-shaped cross section.

Thus for a given position of the tool-holder 21 a needle is gripped in the guide duct 23 between the driven jaw 30 and the driving jaw 40 in exactly the same position whatever its diameter; in other words, the position of the longitudinal axis of said needle does not depend on its diameter. It is therefore possible to change needle during an operation and to preserve the same axis of movement in translation of the needle, whatever its diameter.

In FIGS. 7 and 8 the guide device 20 is represented with a mechanism 80 for locking the needle guide 22 in the guiding position.

The locking mechanism 80 is configured to lock one of the jaws, preferably the driving jaw 40, against rotation if the latter pivots beyond a predetermined angular position. The predetermined angular position corresponds to the position of the jaws when they are in the guiding position.

Immobilising the driving jaw 40 against rotation consequently enables prevention of pivoting of the driven jaw 30 by virtue of the transmission member coupling the jaws to one another.

The locking mechanism 80 advantageously makes it possible for the needle to be held by the driven jaw 30 and the driving jaw 40 and more particularly to prevent angular relative movement of the needle whilst allowing movement in translation along its longitudinal axis.

Any accidental transverse solicitation of the needle is therefore unable to lead to movement of the needle that would be liable to disengage the needle from the guide duct and in the end to injure the patient.

The locking mechanism 80 includes a pivot connection connecting the manipulation handle 49 to the driving jaw 40. The manipulation handle 49 is therefore free to pivot relative to said driving jaw 40 between two extreme angular positions hereinafter termed the "blocking position" and the "unblocking position".

The manipulation handle 49 advantageously includes a shoulder configured to cooperate with a shoulder of the driving jaw 40 so as to prevent rotation of the manoeuvring handle relative to the driving jaw 40 when it pivots toward its unblocking position, as can be seen in the FIGS. 8 and 9 sectional views. These shoulders form a first angular abutment.

The manipulation handle 49 and the driving jaw 40 may equally be conformed so as to cooperate with one another so as to prevent rotation of said manipulation handle 49 relative to the driving jaw 40 when it pivots toward its blocking position so as to form a second angular abutment that can be seen in FIG. 7.

In the locking mechanism example represented in FIGS. 7 to 9 a lip 81 extends from the manipulation handle 49 toward the tool-holder 21.

When the manipulation handle 49 occupies the blocking position the lip 81 is intended to come to rest bearing against a surface of the tool-holder 21. To this end the tool-holder 21 includes a contact surface 215 intended to receive said lip 81 when bearing on it.

The contact surface 215 preferably has a substantially concave cross section and extends for example from a cavity in the tool-holder 21 as far as a protuberance, as FIGS. 7 to 9 show.

The tool-holder 21 is configured so that when the driven jaw 30 and the driving jaw 40 are in the disengaged position the lip 81 is engaged in the cavity. The cavity is therefore in line with the angular travel of the lip 81.

As FIGS. 7 to 9 show, the manipulation handle 49 may comprise an opening 490 through which the protuberance of the tool-holder is introduced when the driven jaw 30 and the driving jaw 40 move toward their disengaged position.

The locking mechanism 80 advantageously includes an elastic member 82 urging said handle in rotation toward its blocking position so that the lip 81 is braced against the contact surface 215 of the tool-holder 21 when the driven jaw 30 and the driving jaw 40 are in the guiding position.

The elastic member 82 is preferably formed by a torsion spring arranged between the driving jaw 40 and the manipulation handle.

This locking mechanism 80 is advantageously effective whatever the diameter of the needle engaged in the guide duct.

Furthermore, this feature enables immobilisation of the needle guide in the guiding position by simple mechanical means.

Another advantage lies in the rapid unblocking of the needle guide to allow it to move into the disengaged position.

In fact, in order to reduce and/or to overcome the friction that is the source of the bracing phenomenon it is merely necessary to apply to the manipulation handle a force opposing the solicitation of the elastic member.

The features described above may advantageously suit both embodiments of the guide device 20 according to the present invention.

The guide device 20 may advantageously include an optical navigation system (not shown in the figures) intended to be connected to a control unit of the robotic arm 10 determining on the basis of information transmitted by said optical navigation system the position of the first jaw 30 and the second jaw 40 relative to one another.

The control unit is configured to control the movements of the robotic arm 10 and therefore the movements of the needle guide 22 as a function of the position of the first jaw 30 and the second jaw 40 relative to one another.

The optical navigation system includes reference optical elements such as spheres the surface of which is reflective.

The spheres are carried by branches extending from the upper end 31, 41 of each of the first jaw 30 and the second jaw 40.

The optical navigation system also includes a reading module transmitting to the control unit information relating to the position in space of each reference optical element.

The first jaw 30 more particularly includes an individual reference optical element and the second jaw 40 more particularly includes at least one pair of reference optical elements. The pair of reference optical elements is carried by a pair of branches extending from a common branch by means of which they are fixed to the mobile jaw 40.

On the basis of the information received by the reading module, the control unit is able to determine the position of the pair of reference optical elements relative to the individual reference optical element and deduce therefrom the positions of the first jaw 30 and the second jaw 40 relative to one another.

The control unit is configured so that if it determines that the first jaw 30 and the second jaw 40 are in the guiding position it prevents movement of the robotic arm 10. It is therefore not possible to modify the position of the guide duct 23 and consequently to move the axis of movement in translation of a needle inserted in said duct or to release the needle laterally from the guide.

This feature enables preservation of the position of the guide device 20 and therefore of the guide duct 23 during a medical operation so as to guarantee the accuracy of the insertion of the needle into a target anatomical zone of the patient.

Furthermore, this feature makes it possible to avoid accidents liable to be caused by the movement of a needle inserted in a needle guide 22.

The control unit is furthermore configured so that if it determines that the first jaw 30 and the second jaw 40 are in the disengaged position it allows movement of the robotic arm 10. It is then possible to move said robotic arm 10 laterally of a target anatomical zone of the patient so as to disengage the needle from the needle guide 22 without contact with the guide device 20. The needle therefore remains immobile during its disengagement.

This feature makes it possible to prevent accidents liable to be caused by the movement of a needle inserted in a target anatomical zone.

More generally, it is to be noted that the embodiments and applications of the invention considered hereinabove have been described by way of nonlimiting example and therefore that other variants may be envisaged.

The invention claimed is:

1. A guide device for guiding a needle, comprising a tool-holder intended to be fixed to the end of a medical assistance robotic arm, said tool-holder supporting a needle guide, wherein the needle guide comprises a first jaw and a second jaw each including a respective groove, said grooves extending along parallel longitudinal axes, said first jaw and said second jaw being supported by the tool-holder so as to allow mobility in rotation of said first jaw and said second jaw relative to one another between a guide position in which the grooves are adjacent and define a duct for guiding the needle and a disengaged position in which the grooves are moved away from one another and define a needle lateral disengagement zone;

wherein the tool-holder comprises a housing extending longitudinally between two end openings and in which the needle guide is engaged, said tool-holder comprising an axial through-opening extending between said end openings along an axis parallel to the longitudinal axis of the housing, the axial through-opening facing the lateral disengagement zone when the first jaw and the second jaw are in the disengaged position, wherein the first jaw and the second jaw are respectively formed by a fixed jaw and by a mobile jaw, and wherein the fixed jaw is formed in one piece with the tool-holder.

2. The guide device of claim 1, wherein the first jaw or the second jaw comprises a handle for manipulating said first jaw or said second jaw by solicitation, wherein said first jaw or said second jaw is driven in movement relative to the other jaw.

3. The guide device of claim 2, wherein the tool-holder comprises a through-opening extending radially relative to the housing, through which the manipulation handle extends, said opening forming a path guiding the manipulation handle.

4. The guide device of claim 3, wherein the opening includes a portion extending axially relative to the housing, said portion opening onto an upper face of the tool-holder that is flush with one of the end openings of said housing.

5. The guide device of claim 1, wherein the fixed jaw is engaged in the housing, said fixed jaw and said housing having on their respective facing surfaces nesting elements cooperating with one another to immobilize said fixed jaw against rotation relative to the tool-holder.

6. The guide device of claim 5, wherein the nesting elements are formed by respective complementary shape reliefs including:

a relief extending longitudinally on an external surface of the fixed jaw, and a relief extending longitudinally on an internal wall of the housing.

7. The guide device of claim 1, wherein the first jaw and the second jaw are removably fixed to one another and are removably engaged in the housing of the tool-holder.

8. The guide device of claim 7, further comprising a sensor housed in one of the grooves and configured to determine the length of the travel of a needle through the guide duct when the first jaw and the second jaw are in the guiding position.

9. The guide device of claim 1, wherein the first jaw and the second jaw include a respective axial shoulder, the axial shoulders having complementary profiles by means of which they cooperate with one another.

10. The guide device of claim 9, wherein the first jaw and the second jaw are removably interconnected by means of a rod extending longitudinally from either the first jaw or the second jaw through an axial housing formed in the axial shoulder of the other jaw.

11. The guide device of claim 1, wherein the guide position is configured guiding the needle along a translation axis while inserting the needle into a target zone and wherein the disengaged position is configured to release the needle after the needle has been inserted into the target anatomical zone.

12. A guide device for guiding a needle, comprising a tool-holder intended to be fixed to the end of a medical assistance robotic arm, said tool-holder supporting a needle guide, wherein the needle guide comprises a first jaw and a second jaw each including a respective groove, said grooves extending along parallel longitudinal axes, said first jaw and said second jaw being supported by the tool-holder so as to allow mobility in rotation of said first jaw and said second jaw relative to one another between a guide position in which the grooves are adjacent each other and define a duct for guiding the needle and a disengaged position in which the grooves are moved away from one another and define a needle lateral disengagement zone;

wherein the needle guide includes a movement transmission member connected to the first jaw and the second jaw and synchronizing the angular movement of said first jaw and said second jaw relative to one another; and wherein each first jaw and each second jaw includes at least one tooth at the level of the grooves, said at least one tooth being adapted to interpenetrate when the needle guide is in the guiding position; and an elastic member arranged against at least one of the jaws so as to urge the first jaw and the second jaw in rotation toward their guiding position.

13. The guide device of claim 12, wherein one of the first jaw and the second jaw comprises a handle configured to manipulate the first jaw or the second jaw, wherein the movement of the first jaw or the second jaw manipulated by the handle is relative to a position of the other of the first jaw and the second jaw.

14. The guide device of claim 12, wherein the movement transition member is formed by two meshing toothed wheel portions respectively arranged on the first jaw and the second jaw or formed by a cam mechanism in which a male part extending from one of the first jaw and the second jaw cooperates with a female part extending from the other of the first jaw and the second jaw.

15. The guide device of claim 14, wherein the locking mechanism includes:

a pivot connection connecting the manipulation handle to the first jaw or to the second jaw and allowing one degree of freedom in rotation of said handle relative to said jaw between two extreme angular positions, a lip extending from the manipulation handle toward the tool-holder, and an elastic member soliciting said handle in rotation toward one of its extreme angular positions so that the lip is braced against a contact surface of the tool-holder when the first jaw and the second jaw are in the guiding position.

16. The guide device of claim 12, wherein the grooves have a V-shape cross-section.

17. The guide device of claim 12, further comprising a mechanism for locking the needle guide in the guiding position, said locking mechanism being configured to immobilize the first jaw or the second jaw against rotation when the latter pivots beyond a predetermined angular position.

18. The guide device of claim 12, further comprising an optical navigation system including reference optical elements mechanically denoted to each of the first jaw and the second jaw and a reading module determining the position of each reference optical element, said navigation system being intended to be connected to a control unit configured to determine on the basis of information relating to the position of the optical elements transmitted by said optical navigation system the position of said first jaw and said second jaw.

19. The guide device of claim 12, wherein the control unit is configured so that:

when the control unit determines that the first jaw and the second jaw are in the guiding position, the control unit prohibits all movement of the robotic arm, and when the control unit determines that the first jaw and the second jaw are in the disengaged position, the control unit allows movement of the robotic arm.

20. A robotic arm comprising at one of its ends the guide device of claim 12, said robotic arm comprises a control unit intended to be receive information relating to a position of the first jaw or of the second jaw from an optical navigation system of the needle guide device, said control unit being configured to determine the position of said jaw and to command the configuration of the robotic arm in a given position according to the determined position of said jaw.

* * * * *